(12) United States Patent
Pan

(10) Patent No.: US 8,968,804 B2
(45) Date of Patent: Mar. 3, 2015

(54) METHODS FOR MANAGING WEIGHT LOSS AND BODY MASS

(71) Applicant: Nestec SA, Vevey (CH)

(72) Inventor: Yuanlong Pan, Chesterfield, MO (US)

(73) Assignee: Nestec SA, Vevey (CH)

( * ) Notice: Subject to any disclaimer, the term of this patent is extended or adjusted under 35 U.S.C. 154(b) by 0 days.

(21) Appl. No.: 13/973,251

(22) Filed: Aug. 22, 2013

(65) Prior Publication Data

US 2014/0056851 A1    Feb. 27, 2014

Related U.S. Application Data

(60) Provisional application No. 61/692,385, filed on Aug. 23, 2012.

(51) Int. Cl.
*A23K 1/18*       (2006.01)
*G09B 19/00*    (2006.01)

(52) U.S. Cl.
USPC .............................................. 426/2; 434/127

(58) Field of Classification Search
USPC .............................................. 426/2; 434/127
See application file for complete search history.

(56) References Cited

U.S. PATENT DOCUMENTS

| | | |
|---|---|---|
| 8,029,819 B2 | 10/2011 | Bierer et al. |
| 2006/0275506 A1 | 12/2006 | Fisher et al. |
| 2011/0165125 A1 | 7/2011 | Pan |

OTHER PUBLICATIONS

International Search Report for PCT/US2013/056150 dated Jan. 24, 2014.
Kresta, J et al, "Effects of Intermittent Dieting During Resistance Training in Women I: Weight Loss and Energy Expenditures" [poster] 2011 American College of Sports Medicine Annual Meeting: 2011, retrieved on Dec. 30, 2013] retrieved from the Internet: <URL: http://exerciseandsportnutritionlab.com/Portals/70/2011%20ACSM%20Posters.pdf>; abstract, lines 3-4; rational lines 7-9; experimental design, lines 7-17.
Kreider, RB et al., "A Structured Diet and Exercise Program Promotes Favorable Changes in Weight Loss, Body Composition, and Weight Maintenance," Journal of the American Dietetic Association, Jun. 2011, vol. 111, Issue 6; pp. 828-843; entire document.
Oliver, J et al., "Comparative effectiveness of two popular weight loss programs in women III; health and fitness markers," Journal of the International Society of Sports Nutrition, 2011, vol. 8, (Supplement 1): P5; entire document.

*Primary Examiner* — Rosanne Kosson
(74) *Attorney, Agent, or Firm* — Ronald A. Burchett; Julie M. Lappin

(57) ABSTRACT

The invention provides methods for promoting weight loss by an animal, promoting weight loss by an animal while preventing or minimizing loss of lean body mass by the animal, preventing a reduction in energy metabolism by an animal, reducing the risk of regaining weight by an animal after weight loss, and ameliorating undesirable animal behaviors associated with reduced caloric intake by intermittently feeding an animal a first diet containing calories that meet the animal's maintenance energy requirements and a second diet containing calories that do not meet the animal's maintenance energy requirements. In preferred embodiments, the described feeding pattern and diets are fed in conjunction with one or more weight loss agents.

11 Claims, No Drawings

METHODS FOR MANAGING WEIGHT LOSS AND BODY MASS

CROSS-REFERENCE TO RELATED APPLICATIONS

This application claims priority to U.S. Provisional Application No. 61/692,385 filed Aug. 23, 2012, the disclosure of which is incorporated herein by this reference.

BACKGROUND OF THE INVENTION

1. Field of the Invention

The invention relates generally to methods for preserving lean body mass and maintaining higher energy expenditure during weight loss and particularly to methods for using feeding patterns for for promoting weight loss while preserving lean body mass and maintaining higher energy expenditure.

2. Description of Related Art

When managing an animal's weight, particularly promoting weight loss, it is a very common practice to reduce calorie intake by restricting the amount of food available to the animal on a chrome and daily basis. Generally, restricting daily food intake chronically causes the animal to be hungry. Hanger is an unpleasant state that often causes one or more unwanted behaviors by the hungry animal, e.g., begging, seeking food, binge eating, and the like. In addition, managing weight loss by chronic and daily caloric reduction may cause undesirable results that affect body composition. Animals that lose weight often lose both fat body mass and lean body mass and reduce their daily energy expenditure. Reduced daily energy-expenditure caused by chronic daily caloric reduction during weight, loss makes animals to regain their lost weight easily and makes it very difficult for the animals to maintain their ideal body weight alter weight loss. Therefore, it is frequently more desirable when losing weight, to lose excess fat body mass while preserving as much lean body mass as possible and maintaining higher daily energy expenditure.

Methods for managing weight loss and body mass are known in the art. For example, U.S. Pat. No. 8,158,683 discloses using extracts of aroma to promote weight loss, U.S. Pat. No. 8,143,215 discloses promoting weight loss by applying satiety-enhancing or appetite-suppressing composition comprising tastant onto food, U.S. Pat. No. 7,989,009 discloses a method for promoting weight loss using black tea extract, white tea extract, guarana extract, oolong tea extract, green mate extract, thiamine, choline and N-acetylcysteine. U.S. Pat. No. 6,204,291 discloses a process for promoting weight loss in overweight dogs using L-camitine. U.S. Pat. No. 7,744,930 discloses compositions, methods and kits for enhancing weight loss while inhibiting loss of lean body mass that use soy protein and chromium in form of salt or chelate. US20040077556A1 discloses methods for promoting weight loss and lean muscle mass using epigallocatechin gallate, caffeine, and 1-tyrosine. U.S. Pat. No. 7,850,997 discloses methods of enhancing lean body mass and exercise performance using L-arganine alpha amino n-butyrate. U.S. Pat. No. 5,804,596 discloses a method for using forskohlin for promoting lean body mass and treating mood disorders. US20070082026A1 discloses methods for reducing caloric intake and controlling weight using dietary fiber. U.S. Pat. No. 8,226,973 discloses using isoflavones for reducing accumulation of body fat in male mammals. US20110281245A1 discloses a system for regulating caloric intake by managing food dishes. US20100109876A1 discloses devices, systems, and methods for controlling caloric intake by modifying consumer behavior. US20030072846A1 discloses packages useful for controlling dietary caloric intake, US20100126588A1 discloses a programmed intermittent, automatic watering system for animals.

These methods are often at least partially effective for managing weight loss and/or lean body mass and related conditions. However, these methods may still result in reduced daily expenditure, and hunger and its undesirable behavioral, side effects. There is, therefore, a need for new methods for promoting weight loss, particularly while preserving lean body mass and maintaining higher energy expenditure, that avoid, at least in part, the undesirable behaviors and reduced daily energy expenditure associated with weight loss achieved by reducing daily caloric intake chronically.

SUMMARY OF THE INVENTION

It is, therefore, an object of the invention to provide methods for preserving lean body mass during weight loss.

It is another object of the invention to provide methods for maintaining higher energy expenditure during weight loss.

It is another object of the invention to provide methods for avoiding at least some of the undesirable animal behaviors associated with weight loss achieved by reducing caloric intake.

It is another object of the invention to provide methods for reducing the risk of regaining weight after a weight loss.

One or more of these and other objects are achieved using novel methods for preserving lean body mass during weight loss by an animal preventing a reduction in daily energy expenditure by an animal, reducing the risk of regaining weight by an animal after weight loss, and ameliorating undesirable animal behaviors associated with reduced caloric intake. The methods involve intermittently feeding an animal a first diet containing calories that meet the animal's maintenance energy requirements and a second diet containing calories that do not meet the animal's maintenance energy requirements or intermittently feeding an animal a first diet containing calories that do not meet, the animal's maintenance energy requirements and a second diet containing calories that meet the animal's maintenance energy requirements. Surprisingly, the animal loses essentially the same amount of weight as if the animal bad been fed only the diet, that does not meet the animal's maintenance energy requirements on a continuous and daily basis. Further, the animal's behavior is more desirable when fed using the feeding pattern, e.g., there is less begging for food, seeking food, binge eating, voracious eating, anxiety, aggression, depression, excessive vocalization, and the like. Similarly, functions often associated with weight loss are beneficially affected, e.g., preventing or minimizing loss of lean body mass by the animal while the animal is losing weight due to reduced caloric intake, preventing a reduction in energy metabolism by an animal while the animal is losing weight due to reduced caloric intake, reducing the risk of regaining weight by an animal after the animal has lost weight.

Other and further objects, features, and advantages of the present invention will be readily apparent to those skilled in the art.

DETAILED DESCRIPTION OF THE INVENTION

Definitions

The term "animal" means a human or other animal that can benefit, from one or methods for promoting weight loss by an animal, promoting weight loss, by an animal while preventing or minimizing loss of lean body mass by the animal, preventing a reduction in energy metabolism by an animal, reducing the risk of regaining weight by an animal after weight loss, and ameliorating, undesirable animal behaviors associated with reduced caloric intake, including avian, bovine, canine, equine, feline, hicrine, murine, ovine, and porcine animals.

The term "companion animal" means domesticated animals such as cats, dogs, rabbits, guinea pigs, ferrets, hamsters, mice, gerbils, horses, cows, goats, sheep, donkeys, pigs, and the like.

The term "intermittent period(s)" or "intermittently" means a first period and a second period of the same of different durations of time that reoccur at defined intervals. For example, daily intermittent periods would involve doing one act for one day, doing a different act on the following day, and possibly repeating the pattern for as many two day periods as needed or desirable. Similarly, one act such as feeding an animal could be done for a week and a second act such as feeding an animal a different diet could be done for two weeks, and the cycle repeated for a year or for the lifetime of the animal. The same would apply for periods of multiple days, weeks, months, quarters, years, and the like, e.g., daily, every other day, every other three days, every other four days, every other five days, every other six days, weekly, every other week, every other two weeks, every other three weeks, monthly, every other month, quarterly, yearly, and the like.

The term "in conjunction" means that an animal is fed for a first period a first diet containing calories that meet the animal's maintenance energy requirements and fed for a second period a second diet containing calories that do not meet the animal's maintenance energy requirements according to the invention and the animal is administered a different compound, composition, or other agent (1) together in dietary composition or (2) separately at the same or different frequency using the same or different administration routes at about the same time or periodically. "Periodically" means that the agent is administered on a dosage schedule acceptable for a specific agent and that the food is fed to an animal routinely as appropriate for the particular animal. "About the same time" generally means that the food and agent are administered at the same time or within about 72 hours of each other. "In conjunction" specifically includes administration schemes wherein agent is administered for a prescribed period and the dietary compositions of the invention are administered indefinitely.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain, life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO).

The term "single package" means that the components of a kit are physically associated in or with one or more containers and considered a unit for manufacture, distribution, sale, or use. Containers include, but are not limited to, bags, boxes, cartons, bottles, packages of any type or design or material over-wrap, shrink-wrap, affixed components (e.g., stapled, adhered, or the like), or combinations thereof. A single package may be containers of individual dietary compositions of the invention physically associated such that they are considered a unit for manufacture, distribution, sale, or use.

The term "Virtual, package" means mat the components of a kit are associated by directions on one or more physical or virtual kit components instructing the user how to obtain the other components, e.g., a bag or other container containing one component and directions instructing the user to go to a website, contact a recorded message or a fax-back service, view a visual message, or contact a caregiver or instructor to obtain instructions on how to use the kit or safety or technical information about one or more components of a kit.

The term "about" means plus or minus 20%, preferably plus or minus 10%, more preferably plus or minus 5%, most preferably plus or minus 2%.

All percentages expressed herein are by weight or amount of the total, weight or amount of the composition unless expressed otherwise.

The invention is not limited to the particular methodology, protocols, and reagents described herein because they may vary. Further, the terminology used herein is for the purpose of describing particular embodiments only and is not intended to limit the scope of the present invention.

As used herein, the singular form of a word includes the plural, and vice versa, unless the context clearly dictates otherwise. Thus, the references "a", "an", and "the" are generally inclusive of the plurals of the respective terms. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed, by law. The discussion of those references is intended merely to summarize the assertions made therein. No admission is made that any such patents, patent applications, publications or references, or any portion thereof, are relevant prior art for the present invention and the right to challenge the accuracy and pertinence of such patents, patent applications, publications, and other references is specifically reserved.

The Invention

In one aspect, the invention provides methods for at least one of preserving lean body mass and preventing or minimizing loss of lean body mass during weight loss by animals, preventing a reduction in energy metabolism and maintaining a higher daily energy expenditure during weight loss by animals, reducing the risk of regaining weight by animals after weight loss, and ameliorating undesirable animal behaviors associated with reduced caloric intake. The methods comprise two feeding periods: caloric reduction period and caloric maintenance period. During the caloric maintenance period, the animals are fed a diet containing calories that meet the animals' maintenance energy requirements. During the caloric reduction, period, the animals are fed with a diet containing calories that do not meet the animals' maintenance energy requirements. The invention is based upon the unexpected discovery that animals fed intermittent feeding patterns will preserve and maintain lean, body mass and maintain a higher energy expenditure while losing same amount of weight as the animals fed low caloric diets continuously, in addition, the animal's behavior will be more desirable, e.g., the animals will not beg for food as often or at all or engage in binge eating as often or at all. Further, when fed according to the invention, the animals will lose weight while preserving lean body mass, retaining energy metabolism characteristic animals that are not losing weight, and not regaining weight that has been lost as a result of reduced caloric intake. Additionally, the methods ameliorate undesirable animal behaviors associated with hunger that results from reduced caloric intake, e.g., begging for food, seeking food, binge eating, voracious eating, anxiety, aggression, depression, excessive vocalization, and the like.

While feeding for a the caloric reduction period and for a caloric maintenance period as described is often sufficient, the preferred methods require that the feeding pattern be repeated for at least two cycles, for several cycles, for as long as the animal benefits from the feeding pattern (e.g., achieves a desired weight loss), or for the life of the animal.

In various embodiments, the caloric reduction period and the caloric maintenance period are periods of the same duration or periods of a different duration, e.g., the caloric reduction period is a one day period and the calorie maintenance period is a two day period. Preferably, the caloric reduction period and the caloric maintenance period are intermittent periods of the same duration.

Generally, the caloric reduction diet contains fewer calories than the caloric maintenance diet in any number of calories sufficient to maintain a higher energy expenditure during weight loss, preserve lean body mass during weight loss, or achieve any related or associated benefit described herein. Preferably the caloric reduction diet contains from five percent (5%) to ninety percent (90%) fewer calories than the caloric maintenance diet, more preferably from ten percent (10%) to seventy percent (70%), most preferably from twenty-percent (20%) to forty (40%). In various embodiments, the calorie reduction diet contains at least five percent (5%), ten percent (10%), fifteen percent (15%), twenty percent (20%), twenty-five percent (25%), thirty percent (30%), forty percent (40%), or fewer calories than the caloric maintenance diet. In specific embodiments, the caloric reduction diet contains less calories than the caloric maintenance diet by in amounts of five percent (5%), ten percent (10%), fifteen percent (15%), twenty percent (20%), twenty-five percent (25%), thirty percent (30%), forty percent (40%), fifty percent (50%), sixty percent (60%), seventy percent (70%), eighty percent (80%), ninety percent (90%) or an amount, between the given percentages. In certain embodiments, the caloric reduction diet contains fewer calories than the caloric maintenance diet in amounts of front about 5% to about 95% of the calories needed to meet the animal's daily maintenance requirement for energy, preferably from about 10% to about 80%, most preferably from about 15% to about 60%. Any suitable amount is acceptable depending upon the desired results.

In one embodiment, the methods of the invention are implemented in conjunction with the administration of one or more weight loss agents. Any weight loss agent that is compatible with, the feeding patterns of the invention can be used in the invention. In various embodiments, the weight loss agent is one or more of carnitine, isoflavones, pyruvate, fish oil, DHA, EPA, fibers, calcium, resistant starch, medium chain triglycerides, green tea extract, phentermine, diethylpropion, orlistat, sibutramine, megestrol, phenylpropanolamine, oxandrolone, oleoylethanolamide, probiotics that promote weight loss, ephedra, conjugated linoleic acid, glucomamian, and the like.

Preferably, the methods are useful for managing weight loss and related, functions described herein for companion animals, particularly those whose diet is controlled by an owner or caregiver. Most preferably, the animals are dogs and cats.

In a further aspect, the invention provides kits suitable for implementing the methods of the invention. The kits comprise in separate containers in a single package or in separate containers in a virtual package, as appropriate for the kit component, (1) a complete and balanced first food composition containing calories that meet an animal's maintenance energy requirements; (2) a complete and balanced second food composition containing calories that do meet the animal's maintenance energy requirements; and (3) instructions for using the food compositions for at least one of promoting weight loss by an animal, promoting weight loss by an animal while preventing or minimizing loss of lean body mass by the animal, preventing a reduction in energy metabolism by an animal, reducing the risk of regaining weight by an animal after weight loss, and ameliorating undesirable animal behaviors associated with reduced caloric intake by feeding the animal for a first period the first food composition and feeding the animal for a second period the second food composition. In certain embodiments, the kits further comprise one or more of one or more weight loss agents.

When the kit comprises a virtual package, the kit is limited to instructions in a virtual environment in combination with one or more physical kit components. Generally, the kit contains the food compositions and other physical components in amounts sufficient to implement the methods of the invention and the virtual package contains the instructions relating to using the physical components to implement the methods of the invention.

In another aspect, the invention provides a means for communicating information about or instructions for one or more of preventing or minimizing loss of lean body mass during weight loss by the animal, preventing a reduction in energy metabolism during weight loss by an animal, reducing the risk of regaining weight by an animal after weight loss, and ameliorating undesirable animal behaviors associated with reduced caloric intake by feeding the animal for caloric maintenance period a caloric maintenance diet containing calories that meet the animal's maintenance energy requirements and feeding the animal for a calorie reduction period a caloric reduction diet containing calories that, do not meet the animal's maintenance energy requirements, and optionally a weight loss agent. The means comprises a document, digital storage media, optical storage media, audio presentation, or visual display containing the information or instructions. In certain embodiments, the communication means is a displayed web site, visual display, brochure, product label package insert, advertisement, handout, public announcement, audiotape, videotape, DVD, CD-ROM, computer readable chip, computer readable card, computer readable disk, computer memory, or combination thereof containing such information or instructions.

Useful information includes one or more of (1) recommended feeding schedules for the animal, particularly based on the animal's species and body condition (e.g., overweight or obese), (2) recommended weight loss agents to be administered in conjunction with the use of the recommended feeding pattern, and (3) contact information for animals or their caregivers to use if they have a question about the invention and its use.

EXAMPLES

The invention can be further illustrated by the following examples, although it will be understood that these examples are included merely for purposes of illustration and are not intended to limit the scope of the invention unless otherwise specifically indicated.

Example 1

Overweight cats were randomized into two (2) groups with 15 cats per group based on baseline body weight, percent body fat, and maintenance energy requirements (MERs).

One group of cats (continuous caloric reduction group; CCR) was fed 75% of their MERs for three months. One group cats (intermittent caloric reduction group; ICR) During each of the three months, eats in the ICR group were fed 75% of their MERs for two weeks (caloric redaction period) and then 100% of their MERs for two weeks (caloric maintenance period), and the pattern was repeated for three months. The cat's body compositions were determined by no-invasive QMR technology. The results are shown in Table 1, Table 2 and Table 3

TABLE 1

Daily caloric intake (g) during the weight loss

| Month | CCR | ICR | % higher caloric intake of ICR over CCR |
|---|---|---|---|
| 1 | 53.58 | 60.82 | 14 |
| 2 | 55.44 | 61.60 | 11 |
| 3 | 56.08 | 62.32 | 11 |
| Average | 55.03 | 61.58 | 12 |

TABLE 2

Changes in Lean Body Mass

| | CCR | ICR |
|---|---|---|
| Lean body mass change in 1$^{st}$ month (g) | −25 | 181 |
| Average lean body mass change in 3 months (g/month) | 71 | 135.3 |

TABLE 3

Changes in Body Fat and Body Weight

| | CCR | ICR |
|---|---|---|
| Body fat Change in 1$^{st}$ month (g) | −257 | −330 |
| Average body fat change in 3 months (g/month) | −417 | −443 |
| Body weight change in 1$^{st}$ month (g) | −360 | −342 |
| Average body weight change in 3 months (g) | 591 | 532 |

Referring to the results, the data show that cats in both groups lost identical body weight and body fat during the experiment even though cats in the ICR group ate 12% more calories than the cats in the CCR group, indicating that the energy expenditure of the eats in the ICR group was at least 12% higher than that of the cats in the CCR group. In other words, cats in the CCR group reduced their daily energy expenditure by at least 12% to compensate for the chrome caloric reduction during the weight loss. However, cats in the ICR group gained 181 g lean body mass while the cats in the CCR group lost 26 g lean body mass at the end of one month of weight loss. During the three months of weight loss, the cats in the ICR group gained an average of 135 g lean body mass, while the cats in the CCR group only gained an average of 71 g lean body mass.

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

What is claimed is:

1. A method for at least one of preserving lean body mass in an animal, minimizing loss of lean body mass during the weight loss by an animal, minimizing a reduction in energy metabolism by an animal, reducing the risk of regaining weight by an animal after weight loss, and ameliorating undesirable animal behaviors associated with reduced caloric intake, the method comprising:
    (a) feeding the animal for a caloric maintenance period a caloric maintenance diet containing calories that meet the animal's maintenance energy requirements; and
    (b) feeding the animal for a caloric reduction period a caloric reduction diet containing calories that do not meet the animal's maintenance energy requirements, wherein the caloric maintenance period and the caloric reduction period are every other day, every other three days, every other four days, every other five days, every other six days, weekly, every other week, every other two weeks, or every other three weeks.

2. The method of claim 1 wherein the feeding for the caloric maintenance period and the feeding for the caloric reduction period are repeated.

3. The method of claim 2 wherein the caloric maintenance period and the caloric reduction period are intermittent periods.

4. The method of claim 1 wherein the caloric maintenance period and the caloric reduction period are periods of the same duration.

5. The method of claim 1 wherein the caloric maintenance period and the caloric reduction period are periods of different duration.

6. The method of claim 1 wherein the caloric reduction diet contains from five percent (5%) to ninety percent (90%) fewer calories than the first diet.

7. The method of claim 1 wherein the caloric reduction diet contains from ten percent (10%) to sixty (60%) fewer calories than the first diet.

8. The method of claim 1 wherein the caloric reduction diet contains from twenty percent (20%) to forty (40%) fewer calories than the first diet.

9. The method of claim 1 wherein the caloric reduction diet contains from about 5 to about 95% of the calories needed to meet the animal's daily maintenance requirement for energy.

10. The method of claim 1 wherein the caloric reduction diet contains from about 10 to about 80% of the calories needed to meet the animal's daily maintenance requirement for energy.

11. The method of claim 1 wherein the caloric reduction diet contains from about 15 to about 60% of the calories needed to meet the animal's daily maintenance requirement for energy.

\* \* \* \* \*

UNITED STATES PATENT AND TRADEMARK OFFICE
CERTIFICATE OF CORRECTION

| | | |
|---|---|---|
| PATENT NO. | : 8,968,804 B2 | Page 1 of 1 |
| APPLICATION NO. | : 13/973251 | |
| DATED | : March 3, 2015 | |
| INVENTOR(S) | : Yuanlong Pan | |

It is certified that error appears in the above-identified patent and that said Letters Patent is hereby corrected as shown below:

In the Specification

Column 3, Line 13. "of the same of" should read "of the same or"

Signed and Sealed this
Nineteenth Day of July, 2016

Michelle K. Lee
*Director of the United States Patent and Trademark Office*